(12) United States Patent
Leboulch et al.

(10) Patent No.: US 8,034,620 B2
(45) Date of Patent: *Oct. 11, 2011

(54) LENTIVIRAL PACKAGING CELLS AND USES THEREFOR

(75) Inventors: Philippe Leboulch, Charlestown, MA (US); Karen Westerman, Reading, MA (US)

(73) Assignee: Bluebird Bio, Inc., Cambridge, MA (US)

( * ) Notice: Subject to any disclaimer, the term of this patent is extended or adjusted under 35 U.S.C. 154(b) by 510 days.

This patent is subject to a terminal disclaimer.

(21) Appl. No.: 11/983,497

(22) Filed: Nov. 9, 2007

(65) Prior Publication Data

US 2008/0187997 A1    Aug. 7, 2008

Related U.S. Application Data

(63) Continuation of application No. 11/099,872, filed on Apr. 5, 2005, now Pat. No. 7,311,907, which is a continuation of application No. 10/112,894, filed on Apr. 1, 2002, now Pat. No. 6,955,919, which is a continuation of application No. 09/311,684, filed on May 13, 1999, now Pat. No. 6,365,150.

(60) Provisional application No. 60/085,283, filed on May 13, 1998.

(51) Int. Cl.
*C12N 15/87* (2006.01)

(52) U.S. Cl. ............... 435/465; 435/69.1; 435/320.1; 435/457; 435/466; 536/23.1; 536/23.4; 536/23.72

(58) Field of Classification Search .................. None
See application file for complete search history.

(56) References Cited

U.S. PATENT DOCUMENTS 6,365,150 B1 * 4/2002 Leboulch et al. ............ 424/93.2
6,955,919 B2 * 10/2005 Leboulch et al. ............ 435/465
7,311,907 B2 * 12/2007 Leboulch et al. ............ 424/93.2

FOREIGN PATENT DOCUMENTS

WO    98/12314 A1    3/1998
WO    98/17815 A1    4/1998

OTHER PUBLICATIONS

Fields, Bernard N. et al, "Fundamental Virology," 3rd Ed. Lippincott-Raven Publishers, pp. 805, 807, 854, 855 (1996).
Richardson, Jennifer H. et al, "Helper virus-free transfer of human immunodeficiency virus type 1 vectors," Journal of General Virology, vol. 76:691-696 (1995).

* cited by examiner

*Primary Examiner* — Zachariah Lucas
*Assistant Examiner* — Michelle S Horning
(74) *Attorney, Agent, or Firm* — Nelson Mullins Riley & Scarborough LLP; Jane E. Remillard, Esq.; Jill Gorny Sloper, Esq.

(57) ABSTRACT

Novel packaging cell lines which produce recombinant retrovirus, free of detectable helper-virus are disclosed. Also disclosed are methods of making the cell lines and methods of producing recombinant retroviruses from the cell lines. Retroviruses produced by the cell lines include lentiviruses, such as HIV, capable of transferring heterologous DNA to a wide range of non-dividing cells. The packaging cells contain at least three vectors which collectively encode retroviral gag, pol, and env proteins, wherein the gag and pol genes are separated, in part, onto two or more different vectors. This is made possible by fusing Vpr or Vpx to pol proteins separated from gag so that the proteins are targeted to assembling virions. Among other advantages, the packaging cells provide the benefit of increased safety when used in human gene therapy by virtually eliminating the possibility of molecular recombination leading to production of replication competent helper virus.

14 Claims, 5 Drawing Sheets

SEQUENCE LISTING

```
<160> NUMBER OF SEQ ID NOS: 2

<210> SEQ ID NO 1
<211> LENGTH: 8
<212> TYPE: PRT
<213> ORGANISM: Human immunodeficiency virus

<400> SEQUENCE: 1

Val Ser Gln Asn Tyr Pro Ile Val
  1               5

<210> SEQ ID NO 2
<211> LENGTH: 7
<212> TYPE: PRT
<213> ORGANISM: Human immunodeficiency virus

<400> SEQUENCE: 2

Ala Arg Val Leu Ala Glu Ala
  1               5
```

LENTIVIRAL PACKAGING CELLS AND USES THEREFOR

RELATED APPLICATIONS

This application is a Continuation application of U.S. Patent application Ser. No. 11/099,872, filed Apr. 5, 2005 (now U.S. Pat. No. 7,311,907), which is a Continuation application of U.S. patent application Ser. No. 10/112,894, filed Apr. 1, 2002 (now U.S. Pat. No. 6,955,919), which is a Continuation application of U.S. application Ser. No. 09/311,684 filed on May 13, 1999 (now U.S. Pat. No. 6,365,150), which claims priority to U.S. Provisional Patent Application No. 60/085,283, filed May 13, 1998, the entire contents of which are hereby incorporated by reference herein.

BACKGROUND OF THE INVENTION

The success of gene therapy techniques depends largely on the ability to achieve a combination of stable chromosomal integration and high-level, regulated expression of transferred genes in a manner safe to humans. Many current techniques allow efficient transient transfection of cells in vitro and in vivo with large DNA fragments. However, subsequent chromosomal integration is very inefficient. To overcome low levels of integration, retroviral vectors, which integrate very efficiently in permissive cells, can be used.

While recombinant retroviral vectors allow for integration of a transgene into a host cell genome, most retroviruses can only transduce dividing cells, which limits their use for in vivo gene transfer to nonproliferating cells such as hepatocytes, myofibers, hematopoietic stem cells, and neurons. Non-dividing cells are the predominant, long-lived cell type in the body, and account for most desirable targets of gene transfer, including liver, muscle, and brain. Even protocols attempting the transduction of hematopoietic stem cells require demanding ex vivo procedures for triggering cell division in these cells prior to infection.

One way of overcoming this obstacle is to employ lentiviral vectors, in place of conventional retroviral vectors. Lentiviruses are complex retroviruses which, based on their higher level of complexity, can integrate into the genome of nonproliferating cells and modulate their life cycles, as in the course of latent infection. These viruses include HIV-1, HIV-2 and SIV. Like other retroviruses, lentiviruses possess gag, pol and env genes which are flanked by two long terminal repeat (LTR) sequences. Each of these genes encodes multiple proteins, initially expressed as one precursor polyprotein. The gag gene encodes the internal structural (matrix capsid and nucleocapsid) proteins. The pol gene encodes the RNA-directed DNA polymerase (reverse transcriptase, integrase and protease). The env gene encodes viral envelope glycoproteins and additionally contains a cis-acting element (RRE) responsible for nuclear export of viral RNA. The 5' and 3' LTRs serve to promote transcription and polyadenylation of the virion RNAs. The LTR contains all other cis-acting sequences necessary for viral replication. Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins. A comprehensive review of lentiviruses, such as HIV, is provided, for example, in *Field's Virology* (Raven Publishers), eds. B. N. Fields et al., © 1996.

In addition to gag, pol, and env, lentiviruses, unlike other retroviruses, have several "accessory" genes with regulatory or structural function. Specifically, HIV-1 possesses at least six such genes, including Vif, Vpr, Tat, Rev, Vpu and Nef. The closely related HIV-2 does not code for Vpu, but codes for another unrelated protein, Vpx, not found in HIV-1.

The Vpr gene encodes a 14 kD protein (96 amino acids) (Myers et al. (1993) *Human Retroviruses and AIDS*, Los Alamos National Laboratory, N.M.). The Vpr open reading frame is also present in most HIV-2 and SIV isolates. Amino acid comparison between HIV-2 Vpr and Vpx shows regions of high homology suggesting that Vpx may have arisen by duplication of the Vpr gene (Myers et al. (1993), supra.). Vpr and Vpx are present in mature viral particles in multiple copies, and have been shown to bind to the p6 protein which is part of the gag-encoded precursor polyprotein involved in viral assembly (WO 96/07741; WO 96/32494). Thus, incorporation of Vpr and Vpx into viral particles occurs by way of interaction with p6 (Lavallee et al. (1994) *J. Virol.* 68: 1926-1934; and Wu et al. (1994) *J. Virol.* 68:6161). It has been further shown that Vpr associates, in particular, with the carboxy-terminal region of p6. The precise role of Vpr and Vpx is yet to be clearly determined, however the data to date suggests that these proteins have a role in the stage of early infection. It has also been shown that Vpr and Vpx, expressed in trans with respect to the HIV genome, can be used to target heterologous proteins to HIV virus (WO 96/07741; WO 96/32494). A description of the structure and function of Vpr and Vpx, including the full-length nucleotide and amino acid sequences of these proteins and their binding domains are also provided in WO 96/07741, as well as in Zhao et al. (1994) *J. Biol. Chem.* 269(22):1577 (Vpr); Mahalingham et al. 91995) *Virology* 207:297 (Vpr); and Hu et al. (1989) *Virology* 173:624) (Vpx). Other relevant references relating to Vpr include, for example, Kondo et al. (1995) *J. Virol.* 69:2759; Lavallee et al. (1994) *J. Virol.* 68:1926; and Levy et al. (1993) *Cell* 72:541. Other relevant references relating to Vpx include, for example, Wu et al. (1994) *J. Virol.* 68:6161. All of the aforementioned publication are incorporated by reference herein.

In view of the advantages associated with retroviral vectors in gene therapy, particularly lentiviruses which are capable of infecting non-dividing cells, improved methods for generating pure stocks of recombinant virus, free of replication-competent helper virus, would be of great value in the art. Recombinant retroviruses are generally produced by introducing a suitable proviral DNA vector into mammalian cells ("packaging cells") that produce the necessary viral proteins for encapsidation of the desired recombinant RNA, but which lack the signal for packaging viral RNA (ψ sequence). Thus, while the required gag, pol, and env genes of the retrovirus are intact, there is no release of wild-type helper virus by these packaging lines. However, when the cells are transfected with a separate vector containing the ψ sequence required for packaging, wild-type retrovirus can arise by recombination (Mann et al. (1983) *Cell* 33:153). This is a major danger, particularly in the case of lentiviruses, such as HIV.

Current approaches to avoid the safety dangers associated with recombination leading to production of replication-competent helper virus include making additional mutations (e.g., LTR deletions) in the viral constructs used to create packaging lines, and separating the viral genes necessary for producing virions onto separate plasmids. For example, it has recently been shown that recombinant Moloney murine leukemia virus (MuLV), free of detectable helper-virus, can be produced by separating the gag and pol genes from the env gene in packaging cells (Markowitz et al. (1998) *J. Virol.* 62(4):1120). These packaging cells contained two separate plasmids collectively encoding the viral proteins necessary for virion production, reducing the likelihood that the recombination events necessary to produce intact retrovirus (i.e., between three plasmid vectors) would occur when cotransfected with a third vector containing the ψ packaging signal.

Additional methods for producing safer retroviral packaging cell lines, particularly lentiviral packaging cell lines, which generate recombinant retrovirus, yet do not themselves either yield detectable helper virus or transfer viral genes, would be of great value in human gene therapy.

SUMMARY OF THE INVENTION

The present invention provides novel packaging cell lines which produce recombinant retrovirus, free of detectable helper-virus. Retroviruses produced by the cell lines of the invention include lentiviruses, such as HIV, capable of transferring heterologous DNA to a wide range of non-dividing cells. Among other advantages, the packaging cells provide the benefit of increased safety when used in human gene therapy by virtually eliminating the possibility of molecular recombination leading to production of replication-competent helper virus.

In one embodiment, the invention provides a retroviral packaging cell line containing at least three separate expression vectors which collectively encode gag, pol, and env polyproteins and which, unlike other packaging cell lines, separate the gag and pol genes, at least in part, onto different vectors to reduce the likelihood of recombination with other retroviral vectors within the cell, leading to the production of replication-competent helper virus. The first vector, referred to as pgag^pol, encodes the complete gag polyprotein (containing viral matrix, capsid and nucleocapsid proteins, such as p17, p24, p9 and p6) and, in certain embodiments, also encodes a portion of the pol polyprotein (containing viral polymerase proteins, such as protease, reverse transcriptase and integrase). In one embodiment, the portion of pol encoded along with gag in the first vector includes the protease (PR) protein. In most lentiviral genomes, PR is encoded by a region of pol which overlaps with gag (see FIG. 5). Therefore, in this embodiment, the first vector encodes gag and the portion of pol which overlaps with gag in the lentiviral (e.g., HIV) genome. Other overlapping or non-overlapping portions of pol can also be included with gag on the first vector. However, in another embodiment, gag and pol are completely separated so that the first vector encodes all of gag and no portion of pol.

The second vector, referred to as pVpr-RTIN, complements the first vector, pgag^pol, by encoding the remaining portion(s) of the pol polyprotein not encoded by pgag^pol. The pol polyprotein includes protease (PR), reverse transcriptase (RT) and integrase (IN). Thus, in the case where pgag^pol encodes PR, the second vector preferably encodes RT and IN. In addition, the second vector encodes a targeting protein which targets the encoded pol proteins (e.g., RT and IN) to assembling virions at the inner face of the plasma membrane. Normally, pol is directed to assembling virions via gag since they are expressed together as one large gag-pol precursor polyprotein (e.g., Pr160$^{gag-pol}$). However, in the vectors of the present invention, gag and at least a portion of pol are separated onto different vectors. Thus, the invention employs an agent which targets the portion of pol encoded by the second vector to assembling virions. The targeting agent (e.g., protein or peptide) is preferably encoded in frame with the portion of pol, so that the vector is expressed as a single fusion protein.

Any suitable targeting agent which binds to a component of assembling retroviral virions (e.g., lentiviral gag proteins) can be encoded (e.g., along with a portion of pol) by the second vector. Suitable targeting agents include, for example, antibodies, antibody fragments, proteins and peptides. In one embodiment, the targeting protein is either Vpr or Vpx, including fragments or mutants thereof, which bind to p6 gag protein. Thus, in one embodiment, the second vector encodes a Vpr or Vpx fusion protein containing Vpr or Vpx (or peptides, mutants or variants thereof) and a portion of pol, where the portion of pol preferably includes RT and IN. Within this fusion construct, RT and IN are preferably preceded by a protease cleavage site so that they are cleaved and activated by PR once they become associated with assembling virions.

The third vector, referred to as pENV, encodes a viral env which provides one or more envelope proteins for viral particles encoded by the first and second vectors. In one embodiment, the viral env is from a lentivirus, such as HIV, SIV, FIV, EIV (e.g., gp120 and gp41). In another embodiment, the viral env is from VSV (e.g., VSV-G glycoprotein which pseudotypes the recombinant retroviral particles encoded by the first and second vectors). In yet another embodiment, the viral env is from a Type C retrovirus, such as MoMuLV, HaMuSV, MuMTV, GaLV, FLV and RSV.

The first, second and third vectors described above are cotransfected into suitable packaging cells, such as 293T human kidney cells, to produce novel packaging cell lines of the invention. When cotransfected with a fourth vector, which contains the necessary Ψ and LTR sequences for packaging of RNA into viral particles, the cells produce recombinant, helper-free retrovirus. Accordingly, in another embodiment, the invention provides a producer cell line containing a fourth vector (along with the first, second and third vectors), referred to as pΨ. The fourth vector comprises a retroviral packaging signal (Ψ), preferably along with a selected transgene, flanked by long terminal repeat sequences (LTRs). Any of the first, second, third or fourth vectors also can contain an RNA export element, such as the HIV RRE, and/or a marker gene enabling the detection of positive cell transformants, as well as unwanted helper-virus.

In another embodiment, the invention provides a method of producing a packaging cell line capable of generating recombinant, helper-free retrovirus. The method involves transfecting a suitable host cell with a first vector encoding a retroviral gag polyprotein along with (in certain embodiments) a portion of a retroviral pol protein, a second vector encoding the remainder of the retroviral pol polyprotein not encoded by the first vector fused to a Vpr or a Vpx protein, and a third vector encoding a viral env protein, each as described above. Each one of the first, second or third vectors contains a promoter operably linked to a gene encoding the gag polyprotein, pol polyprotein, Vpr protein, Vpx protein or env protein. In one embodiment, the promoter is an inducible promoter allowing for selective expression of the gag polyprotein, pol polyprotein, Vpr protein, Vpx protein or env protein within the packaging cells.

In yet another embodiment, the invention provides a method of producing a recombinant retrovirus by co-transfecting a host cell with a first vector comprising a retroviral gag gene and (in certain embodiments) a portion of a retroviral pol gene, both operably linked to a promoter; a second vector comprising all or the remaining portion of the retroviral pol gene not contained within the first vector and a gene encoding all or a portion of a Vpr or a Vpx protein, the genes being operably linked to a promoter and expressed as a single fusion protein; a third vector comprising a viral env gene; and a fourth vector comprising a viral packaging signal, a viral long terminal repeat (LTR), and preferably a transgene, all as described above. Following cotransfection of the first, second, third and fourth vectors into suitable cells, recombinant retrovirus can be recovered from the cell culture medium.

Packaging cell lines of the invention, and recombinant retroviruses (e.g., HIV and SIV) produced from these cell lines, can be used to deliver heterologous nucleic acids (e.g., therapeutic transgenes) to dividing and non-dividing cells in a safe and efficient manner. For example, they can be used to transform target cells with a desired DNA in vitro. Additionally, they can be used in vivo to deliver therapeutic genes to cells (e.g., in methods of human gene therapy) without the danger of recombination leading to the producing replication-competent helper-virus.

BRIEF DESCRIPTION OF THE FIGURES

FIG. 1 shows a map of plasmid pgag^pol used in the packaging cell line of the invention. The plasmid contains the CMV promoter upstream of an HIV gag and mutated pol gene. The pol gene is mutated (e.g., by deletion or site directed mutagenesis to alter the coding sequence) to prevent expression of at least a portion of the pol polyprotein, preferably reverse transcriptase (RT) and integrase (IN). Preferably pol is also mutated to prevent expression of accessory genes.

FIG. 2 shows a map of plasmid pVpr-RTIN used in the packaging cell line of the invention. The plasmid contains the inducible RSV-LTR promoter upstream of a Vpr fusion gene encoding Vpr and at least a portion of HIV pol which is mutated in plasmid pgag^pol. Thus, pVpr-RTIN complements the mutated gag^pol coding sequence in pgag^pol. Preferably, pVpr-RTIN encodes a fusion protein containing Vpr, followed by a protease cleavage site immediately upstream from RT and IN, as well as the HIV RNA export element, RRE, placed so that it is transcribed along with the Vpr, RT and IN, all as shown in FIG. 2.

FIG. 3 shows a map of plasmids pENV and pΨ used in the packaging cell line of the invention. Plasmid pENV contains the inducible RSV-LTR promoter upstream of a gene encoding the VSVg glycoprotein. This plasmid provides a pseudotyped envelope protein for the recombinant retrovirus. Plasmid pΨ contains, from 5' to 3', a 5'LTR, the HIV packaging signal (Ψ), an MRNA export element (RRE from HIV), the CMV promoter, a marker gene (GFP), and a 3'LTR. The 5'(left) LTR is preferably a hybrid LTR containing minimal HIV LTR sequences in combination with portions of MuLV LTR or the CMV promoter. The 3'(right) LTR is also preferably a hybrid promoter containing minimal HIV LTR sequences in combination with a non-lentiviral poly A sequence (e.g., from the rabbit β-globin gene).

DETAILED DESCRIPTION OF THE INVENTION

Unlike other retroviral packaging cell lines, the cell lines provided by the present invention contain separate expression vectors encoding at least portions of gag, pol and env polyproteins. By separating all or portions of the gag, pol and env genes onto three separate plasmids, the risk of molecular recombination within the packaging cells to produce replication-competent helper virus is virtually eliminated. Accordingly, the retroviral packaging cells of the invention are safer for use in human gene therapy, in addition to providing the advantages of enabling stable genomic integration of DNA into a wide range of dividing and non-dividing cells.

Definitions

As used herein, the following terms and phrases used to describe the invention shall have the meanings provided below.

The phrase "retroviral packaging cell line" refers to a cell line (typically a mammalian cell line) which contains the necessary coding sequences to produce viral particles which lack the ability to package RNA and produce replication-competent helper-virus. When the packaging function is provided within the cell line (e.g., in trans), the packaging cell line produces recombinant retrovirus, thereby becoming a "retroviral producer cell line."

The term "retrovirus" refers to any known retrovirus (e.g., type c retroviruses, such as Moloney murine leukemia virus (MoMuLV), Harvey murine sarcoma virus (HaMuSV), murine mammary tumor virus (MuMTV), gibbon ape leukemia virus (GaLV), feline leukemia virus (FLV) and Rous Sarcoma Virus (RSV)). "Retroviruses" of the invention also include human T cell leukemia viruses, HTLV-1 and HTLV-2, and the lentiviral family of retroviruses, such as human Immunodeficiency viruses, HIV-1, HIV-2, simian immnodeficiency virus (SIV), feline immonodeficiency virus (FIV), equine immnodeficiency virus (EIV), and other classes of retroviruses.

The terms "gag polyprotein", "pol polyprotein", and "env polyprotein" refer to the multiple proteins encoded by retroviral gag, pol and env genes which are typically expressed as a single precursor "polyprotein". For example, HIV gag encodes, among other proteins, p17, p24, p9 and p6. HIV pol encodes, among other proteins, protease (PR), reverse transcriptase (RT) and integrase (IN). HIV env encodes, among other proteins, Vpu, gp120 and gp41. As used herein, the term "polyprotein" shall include all or any portion of gag, pol and env polyproteins.

The terms "Vpx" and "Vpr" refer respectively to lentiviral Vpx and Vpr proteins described, for example, in WO 96/07741, hereby incorporated by reference in its entirety. These terms also refer to fragments, mutants, homologs and variants of Vpr and Vpx which retain the ability to associate with p6.

The term "fusion protein" refers to a molecule comprising two or more proteins linked together. Typically, the fusion protein is an amino acid sequence comprising two or more protein sequences.

The term "vector" refers to a nucleic acid molecule capable of transporting another nucleic acid to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

The term "transgene" means a nucleic acid sequence (e.g., a therapeutic gene), which is partly or entirely heterologous, i.e., foreign, to a cell into which it is introduced, or, is homologous to an endogenous gene of the cell into which it is introduced, but which is designed to be inserted into the genome of the cell in such a way as to alter the genome (e.g., it is inserted at a location which differs from that of the natural gene or its insertion results in "a knockout"). A transgene can include one or more transcriptional regulatory sequences and any other nucleic acid, such as introns, that may be necessary for optimal expression of a selected nucleic acid.

The terms "transformation" and "transfection" mean the introduction of a nucleic acid, e.g., an expression vector, into a recipient cell.

The term "RNA export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al. (1991) *J. Virol.* 65: 1053; and Cullen et al. (1991) *Cell* 58: 423-426), and the hepatitis B virus post-transriptional regulatory element (PRE) (see e.g., Huang et al. (1995) *Molec. and Cell. Biol.* 15(7):3864-3869; Huang et al. (1994) *J. Virol.* 68(5):3193-3199; Huang et al. (1993) *Molec. and Cell. Biol.* 13(12): 7476-7486), and U.S. Pat. No. 5,744,326). Generally, the RNA export element is placed within the 3' UTR of a gene, and can be inserted as one or multiple copies. RNA export elements can be inserted into any or all of the separate vectors generating the packaging cell lines of the present invention.

Recombinant Retroviral Vectors

Packaging cells of the present invention comprise three or more separate retroviral vectors which respectively encode all or portions of gag, pol and env. Protocols for producing recombinant retroviral vectors, and for transforming packaging cell lines, are well known in the art (*Current Protocols in Molecular Biology*, Ausubel, F. M. et al. (eds.) Greene Publishing Associates, (1989), Sections 9.10-9.14 and other standard laboratory manuals; Eglitis, et al. (1985) *Science* 230: 1395-1398; Danos and Mulligan (1988) *Proc. Natl. Acad Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; 4,980,286; PCT Application WO 89/07136; PCT Application WO 89/02468; PCT Application WO 89/05345; and PCT Application WO 92/07573). Moreover, suitable retroviral sequences which can be used in the present invention can be obtained from commercially available sources. For example, such sequences can be purchased in the form of retroviral plasmids, such as pLJ, pZIP, pWE and pEM. Suitable packaging sequences which can be employed in the vectors of the invention are also commercially available including, for example, plasmids ψCrip, ψCre, ψ2 and ψAm. Thus, while the present invention shall be described with respect to particular embodiments (e.g., particular lentiviral vectors), other retroviral vectors for use in the invention can be prepared in accordance with the guidelines described herein.

In a particular embodiment, the invention provides a packaging cell comprising three or more recombinant lentiviral vectors. These vectors can be prepared by inserting selected lentiviral sequences into a suitable vector (e.g., a commercially available expression plasmid containing appropriate regulatory elements (e.g., a promoter and enhancer), restriction sites for cloning, marker genes etc.). This can be achieved using standard cloning techniques, including PCR, as is well known in the art. Lentiviral sequences to be cloned into such vectors can be obtained from any known source, including lentiviral genomic RNA, or cDNAs corresponding to viral RNA. Suitable cDNAs corresponding to lentiviral genomic RNA are commercially available and include, for example, pNLENV-1 (Maldarelli et al. (1991) *J. Virol.* 65:5732) which contains genomic sequences of HIV-1. Other sources of retroviral (e.g., lentiviral) cDNA clones include the American Type Culture Collection (ATCC), Rockville, Md.

Once cloned into an appropriate vector (e.g., expression vector), retroviral sequences (e.g., gag, pol, env, LTRs and cis-acting sequences) can be modified as described herein. In one embodiment, lentiviral sequences amplified from plasmids, such as pNLENV-1, are cloned into a suitable backbone vector, such as a pUC vector (e.g., pUC19) (University of California, San Francisco), pBR322, or pcDNA1 (InVitrogen, Inc.), and then modified by deletion (using restriction enzymes), substitution (e.g., using site directed mutagenesis), or other (e.g., chemical) modification to prevent expression or function of selected lentiviral sequences. As described in the Examples provided herein, portions of the gag, pol and env genes can be removed or mutated, along with selected accessory genes. For example, in one embodiment, a portion of pol is deleted or otherwise mutated to produce a truncated gag-^pol gene which contains all of gag and a portion of pol.

It is preferable that each vector of the invention contains the minimum lentiviral sequences necessary to encode the desired lentiviral proteins (e.g., gag, pol and env) or direct the desired lentiviral function (e.g., packaging of RNA). That is, the remainder of the vector is preferably of non-viral origin, or from a virus other than a lentivirus (e.g., HIV). In one embodiment, lentiviral LTRs contained in the retroviral vectors of the invention are modified by replacing a portion of the LTR with a functionally similar sequence from another virus, creating a hybrid LTR. For example, the lentiviral 5'LTR, which serves as a promoter, can be partially replaced by the CMV promoter or an LTR from a different retrovirus (e.g., MuLV or MuSV). Alternatively, or additionally, the lentiviral 3' LTR can be partially replaced by a polyadenylation sequence from another gene or retrovirus. In one embodiment, a portion of the HIV-1 3' LTR is replaced by the polyadenylation sequence of the rabbit β-globin gene. By minimizing the total lentiviral sequences within the vectors of the invention in this manner, the chance of recombination among the vectors, leading to replication-competent helper lentivirus, is greatly reduced.

Any suitable expression vector can be employed in the present invention. As described in Examples below, suitable expression constructs include a human cytomegalovirus (CMV) immediate early promoter construct. The cytomegalovirus promoter can be obtained from any suitable source. For example, the complete cytomegalovirus enhancer-promoter can be derived from the human cytomegalovirus (hCMV). Other suitable sources for obtaining CMV promoters include commercial sources, such as Clontech, Invitrogen and Stratagene. Part or all of the CMV promoter can be used in the present invention. Other examples of constructs which can be used to practice the invention include constructs that use MuLV, SV40, Rous Sarcoma Virus (RSV), vaccinia P7.5, and rat β-actin promoters. In some cases, such as the RSV and MuLV, these promoter-enhancer elements are located within or adjacent to the LTR sequences.

Suitable regulatory sequences required for gene transcription, translation, processing and secretion are art-recognized, and are selected to direct expression of the desired protein in an appropriate cell. Accordingly, the term "regulatory sequence", as used herein, includes any genetic element present 5' (upstream) or 3' (downstream) of the translated region of a gene and which control or affect expression of the gene, such as enhancer and promoter sequences. Such regulatory sequences are discussed, for example, in Goeddel, *Gene expression Technology: Methods in Enzymology*, page 185, Academic Press, San Diego, Calif. (1990), and can be selected by those of ordinary skill in the art for use in the present invention.

In one embodiment, the invention employs an inducible promoter within the retroviral vectors, so that transcription of selected genes can be turned on and off. This minimizes cellular toxicity caused by expression of cytotoxic viral proteins, increasing the stability of the packaging cells containing the vectors. For example, high levels of expression of VSV-G (envelope protein) and Vpr can be cytotoxic (Yee, J.-K., et al., Proc. Natl. Acad. Sci., 91:9654-9568 (1994) and, therefore, expression of these proteins in packaging cells of the invention can be controlled by an inducible operator system, such as the inducible Tet operator system (GIBCO-BRL™), allowing for tight regulation of gene expression (i.e., generation of retroviral particles) by the concentration of tetracycline in the culture medium. That is, with the Tet operator system, in the presence of tetracycline, the tetracycline is bound to the Tet transactivator fusion protein (tTA), preventing binding of tTA to the Tet operator sequences and allowing expression of the gene under control of the Tet operator sequences (Gossen et al. (1992) PNAS 89:5547-5551), In the absence of tetracycline, the tTA binds to the Tet operator sequences preventing expression of the gene under control of the Tet operator.

Examples of other inducible operator systems which can be used for controlled expression of the protein which provides a pseudotyped envelope are 1) inducible eukaryotic promoters responsive to metal ions (e.g., the metallothionein promoter), glucocorticoid hormones and 2) the LAC-SWITCH™ Inducible Mammalian Expression System (STRATAGENE™) of *E. coli*. Briefly, in the *E. coli* lactose operon, the Lac repressor binds as a homotetramer to the lac operator, blocking transcription of the lac2 gene. Inducers such as allolactose (a physiologic inducer) or isopropyl-β-D-thiogalactoside (IPTG, a synthetic inducer) bind to the Lac repressor, causing a conformational change and effectively decreasing the affinity of the repressor for the operator. When the repressor is removed from the operator, transcription from the lactose operon resumes.

In yet another approach, selective expression of retroviral genes contained within the vectors of the invention can be achieved by cloning in a Cre/lox repressor system upstream of selected coding sequences. Specifically, a polystop signal can be inserted between the gene(s) to be selectively expressed and a 5' promoter. The polystop signal is flanked by two loxP1 sites (Sauer (1993) Methods in Enzymology 225: 890-900). Upon contact with cre recombinase, the lox sites will recombine and delete the polystop signal, allowing the promoter to act in cis to turn on expression of the gene(s).

Viral Envelope Proteins and Pseudotyping

In addition to encoding the necessary retroviral proteins for production and assembly of core virions (e.g., gag and pol proteins), packaging cell lines of the invention also encode viral envelope proteins (env) which determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Examples of retroviral-derived env genes which can be employed in the invention include, but are not limited to type C retroviral envelope proteins, such as those from Moloney murine leukemia virus (MoMuLV), Harvey murine sarcoma virus (HaMuSV), murine mammary tumor virus (MuMTV), gibbon ape leukemia virus (GaLV), and Rous Sarcoma Virus (RSV). Other viral env genes which can be used include, for example, env genes from immunodeficiency viruses (HIV-1, HIV-2, FIV, SIV and EIV), human T cell leukemia viruses (HTLV-1 and HTLV-3), and Vesicular stomatitis virus (VSV) (Protein G). When producing recombinant retroviruses of the invention (e.g., recombinant lentiviruses), the wild-type retroviral (e.g., lentiviral) env gene can be used, or can be substituted with any other viral env gene, such those listed above. Methods of pseudotyping recombinant viruses with envelope proteins from other viruses in this manner are well known in the art. As referred to herein, a "pseudotype envelope" is an envelope protein other than the one that naturally occurs with the retroviral core virion, which encapsidates the retroviral core virion (resulting in a phenotypically mixed virus).

In one embodiment, the invention provides packaging cells which produce recombinant lentivirus (e.g., HIV, SIV, FIV, EIV) pseudotyped with the VSV-G glycoprotein. The VSV-G glycoprotein has a broad host range. Therefore, VSV-G pseudotyped retroviruses demonstrate a broad host range (pantropic) and are able to efficiently infect cells that are resistant to infection by ecotropic and amphotropic retroviruses. (Yee et al. (1004) *PNAS* 91:9564-9568. Any suitable serotype (e.g., Indiana, New Jersey, Chandipura, Piry) and strain (e.g., VSV Indiana, San Juan) of VSV-G can be used in the present invention. The protein chosen to pseudotype the core virion determines the host range of the packaging cell line. VSV-G interacts with a specific phospholipid on the surface of mammalian cells (Schlegel, R., et al., *Cell,* 32:639-646 (1983); Spuertzi, F., et al., *J. Gen. Virol.,* 68:387-399 (1987)). Thus, packaging cell lines which utilize VSV-G to provide a pseudotyped envelope for the retroviral core virion have a broad host range (pantropic). Moreover, VSV-G pseudotyped retroviral particles can be concentrated more than 100-fold by ultracentrifugation (Burns, J. C., et al., *Proc. Nat'l. Acad. Sci.,* 90:8033-8037 (1993)). Stable VSV-G pseudotyped retrovirus packaging cell lines permit generation of large scale viral preparations (e.g. from 10 to 50 liters supernatant) to yield retroviral stocks in the range of $10^7$ to $10^{11}$ retroviral particles per ml.

Viral envelope proteins of the invention (whether pseudotyped or not) can also be modified, for example, by amino acid insertions, deletions or mutations to produce targeted envelope sequences such as ecotropic envelope with the EPO ligand, synthetic and/or other hybrid envelopes; derivatives of the VSV-G glycoprotein. Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J. Gen Virol* 73:3251-3255; and Goud et al. (1983) *Virology* 163:251-254); or coupling cell surface receptor ligands to the viral env proteins (Neda et al. (1991) *J Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Packaging Cell Lines

Any suitable cell line can be employed to prepare packaging cells of the invention. Generally, the cells are mammalian cells. In a particular embodiment, the cells used to produce the packaging cell line are human cells. Suitable human cell lines which can be used include, for example, 293 cells (Graham et al. (1977) *J. Gen. Virol.*, 36:59-72, tsa 201 cells (Heinzel et al. (1988) *J. Virol.*, 62:3738), and NIH3T3 cells (ATCC)). Other suitable packaging cell lines for use in the present invention include other human cell line derived (e.g., embryonic cell line derived) packaging cell lines and murine cell line derived packaging cell lines, such as Psi-2 cells (Mann et al. (1983) *Cell*, 33:153-159; FLY (Cossett et al. (1993) *Virol.*, 193:385-395; BOSC 23 cells (Pear et al. (1993) *PNAS* 90:8392-8396; PA317 cells (Miller et al. (1986) *Molec. and Cell. Biol.*, 6:2895-2902; Kat cell line (Finer et al. (1994) *Blood*, 83:43-50; GP+E cells and GP+EM12 cells (Markowitz et al. (1988) *J. Virol.*, 62:1120-1124, and Psi Crip and Psi Cre cells (U.S. Pat. No. 5,449,614; Danos, O. and Mulligan et al. (1988) *PNAS* 85:6460-6464). Packaging cell lines of the present invention can produce retroviral particles having a pantropic amphotropic or ecotropic host range. Preferred packaging cell lines produce retroviral particles, such as lentiviral particles (e.g., HIV-1, HIV-2 and SIV) capable of infecting dividing, as well as non-dividing cells.

Cell Transfection and Screening

Recombinant Retroviral vectors of the invention which collectively encode gag, pol and env proteins (necessary for the production of empty viral particles), wherein gag and pol are at least in part separated onto two separate vectors, are co-transfected into suitable cells using standard transfection techniques to create packaging cell lines. Any known cell transfection technique can be employed for this purpose. Generally cells are incubated (i.e., cultured) with the vectors in an appropriate medium under suitable transfection conditions, as is well known in the art. For example, methods such as electroporation and calcium phosphate precipitation (O'Mahoney et al. (1994) *DNA & Cell Biol.* 13(12): 1227-1232) can be used.

Positive packaging cell transformants (i.e., cells which have taken up and integrated the retroviral vectors) can be screened for using a variety of selection markers which are well known in the art. For example, marker genes, such as green fluorescence protein (GFP), hygromycin resistance (Hyg), neomycin resistance (Neo) and β-galactosidase (β-gal) genes can be included in the vectors and assayed for using e.g., enzymatic activity or drug resistance assays. Alternatively, cells can be assayed for reverse transcriptase (RT) activity as described by Goff et al. (1981) *J. Virol.* 38:239 as a measure of viral protein production.

Similar assays can be used to test for the production by packaging cells of unwanted, replication-competent helper virus. For example, marker genes, such as those described above, can be included in the "producer" vector containing the viral packaging sequence (Ψ) and LTRs. Following transient transfection of packaging cells with the producer vector, packaging cells can be subcultured with other non-packaging cells. These non-packaging cells will be infected with recombinant, replication-deficient retroviral vectors of the invention carrying the marker gene. However, because these non-packaging cells do not contain the genes necessary to produce viral particles (e.g., gag, pol and env genes), they should not, in turn, be able to infect other cells when subcultured with these other cells. If these other cells are positive for the presence of the marker gene when subcultured with the non-packaging cells, then unwanted, replication-competent virus has been produced.

Accordingly, to test for the production of unwanted helper-virus, packaging cells of the invention can be subcultured with a first cell line (e.g., NIH3T3 cells) which, in turn, is subcultured with a second cell line which is tested for the presence of a marker gene or RT activity indicating the presence of replication-competent helper retrovirus. Marker genes can be assayed for using e.g., FACS, staining and enzymatic activity assays, as is well known in the art.

Uses in Gene Therapy

Novel packaging cell lines of the invention can be used to produce recombinant retroviruses (e.g., recombinant lentiviruses), free of unwanted helper-virus, which are capable of transferring (and efficiently integrating) heterologous DNAs (e.g., a therapeutic transgene) into eukaryotic cells. That is, recombinant retrovirus can be harvested from packaging cell lines of the invention and used as viral stock to infect recipient cells in culture or in vivo. In the case of secreted proteins or proteins expressed in hematopoietic cells, sensitive assays such as ELISA or Western blotting can be used to assess gene transfer efficiency.

Specifically, recombinant lentiviruses produced by packaging cells of the invention can safely be used to transform not only a variety of dividing cell types, but also non-dividing cell types, increasing the range of diseases treatable by gene therapy. For instance, these recombinant lentiviruses can be used to transform neuron, muscle, heart, lung, liver, skin, and bone marrow cells.

A wide variety of heterologous DNAs can be transferred to cells via the invention. Such DNAs include, for example, therapeutic genes (e.g., encoding therapeutic proteins which can be used to treat diseases). Because non-dividing, as well as dividing, cells can be transformed via recombinant retroviruses (e.g., lentiviruses) of the invention, treatable diseases include, for example, globin disorders, blood coagulation factor deficiency, neural disorders, autoimmune diseases, lung diseases. Thus, suitable therapeutic genes to be transferred can include, for example, human β-globin, Factor VIII, Factor IX and Cystic Fibrosis genes. Alternatively, retroviral vectors of the invention can be used to deliver antisense polynucleotides to cells to inhibit expression of selected genes (Yee, J.-K., et al., *Proc. Natl. Acad. Sci.*, 91:9564-9568 (1994); Dranoff, G., et al., *Proc. Natl. Acad. Sci.*, 90:3539-3543 (1993); Miller, A. D., et al., *Meth. in Enz.*, 217:581-599 (1993)).

In addition, the packaging cell lines of the present invention can also be used to produce retroviruses containing DNA of interest for introducing DNA or genes of interest into mammalian cells, such as human cells, which will subsequently be administered into localized areas of the body (e.g., ex vivo infection of autologous white blood cells for delivery of protein into localized areas the body, see e.g., U.S. Pat. No. 5,399,346).

Equivalents

Those skilled in the art will recognize, or be able to ascertain using no more than routine experimentation, many equivalents to the specific embodiments of the invention described herein. Such equivalents are intended to be encompassed by the following claims. The entire contents of all references, patents and published patent applications cited throughout this application are hereby incorporated by reference.

EXAMPLES

Preparation of Helper Free Lentiviral Packaging Cell Line

Stable packaging cell lines which produce recombinant HIV, free of detectable helper-virus, were prepared as described below. The packaging cell lines virtually eliminate the possibility of recombinational events that can result in intact, replication-competent helper-virus, by separating the necessary coding sequences to produce and assemble virions, and package RNA, onto four separate plasmids, referred to herein as plasmids pgag^pol, pVpr-RTIN, pENV and pψ. These plasmids contain minimal common HIV sequences, and minimal HIV non-coding sequences. They also contain inducible promoters to prevent toxicity to packaging cells caused by expression of cytotoxic proteins, such as Vpr. When transiently co-transfected into suitable mammalian packaging cells, the cells produce HIV-derived retroviral vector particles without recombination to produce helper-virus.

Plasmid Preparation

Each expression plasmid was constructed using standard cloning techniques (Sambrook, J. et al. (1989) *Molecular Cloning: A laboratory Manual*-2nd. Cold Spring Harbor Laboratory Press, Cold Spring Harbor New York, USA). Oligonucleotides for cloning were synthesized using standard protocols, or obtained from commercially available sources, such as GENSET™ Inc. Accuracy of plasmid construction was verified using standard nucleotide sequencing techniques. All plasmids contained suitable promoter sequences, such as the human early cytomegalovirus (hCMV) promoter and, optionally a reporter gene, such as the green fluorescent protein (GFP) gene. Desired lentiviral (e.g., HIV-1) coding and non-coding sequences were obtained by amplifying selected sequences from available plasmids containing proviral DNA, such as PNLENV-1 (Maldarelli et al. (1991) *J. Virol.* 65:5732).

Plasmid pgag^pol

Figure 5:
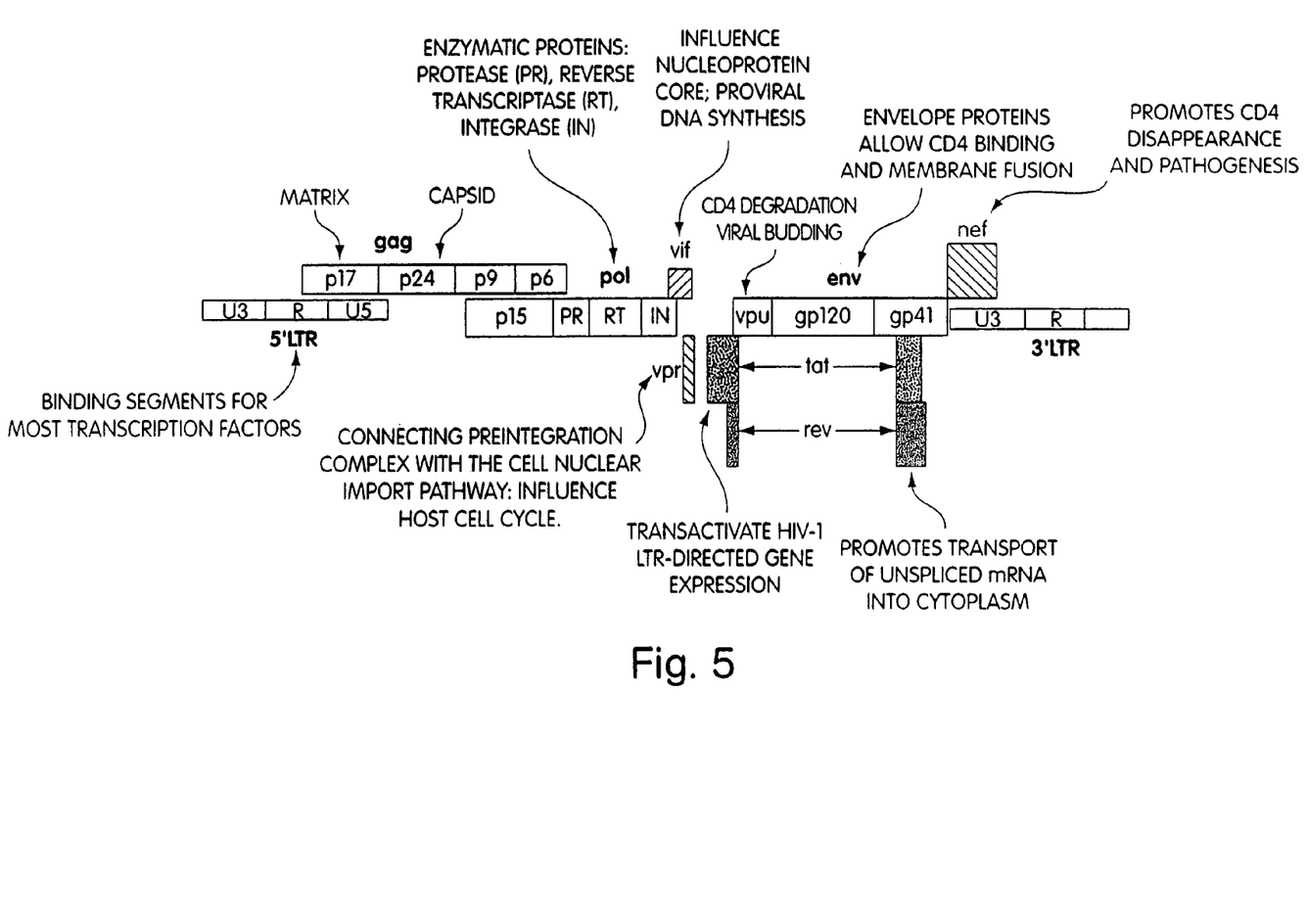
FIG. 5 shows a map of the HIV-1 genome, including the 5'LTR, gag, pol, env, 3'LTR and accessory genes.

Plasmid pgag^pol was designed to encode the gag polyprotein and a portion of the pol polyprotein, preferably the portion of pol which overlaps with gag in the lentiviral genome including, but not limited to, the lentiviral protease (PR) (see e.g., FIG. 5). This was achieved either by deleting a portion of the pol coding sequence, or by mutating a portion of the pol coding sequence so that only a portion of the pol gene was expressed.

Figure 1:
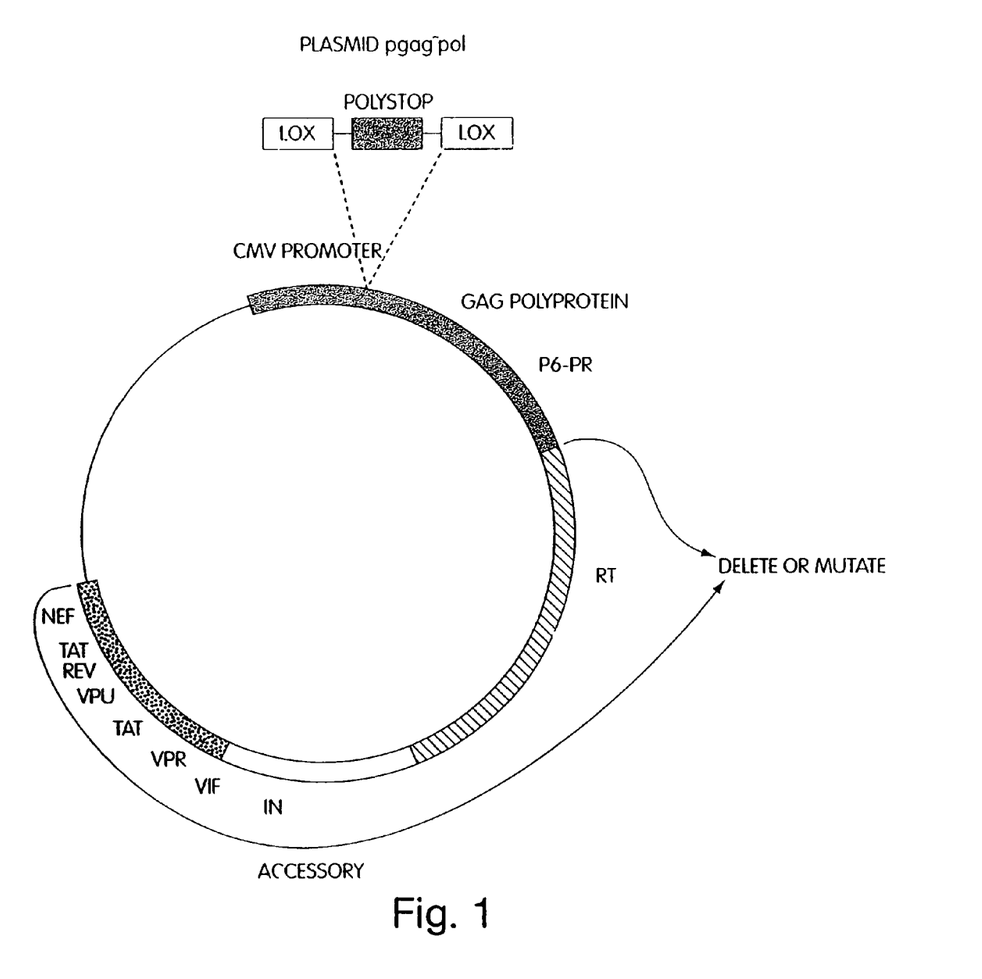

To construct pgag^pol, a cDNA containing the HIV proviral genome, such as PNLENV-1 (Maldarelli et al. (1991) *J. Virol.* 65:5732) (kindly provided by Stephen Goff), was amplified and cloned into one or more suitable expression vectors, such as pCDNA 1 and pCDNA 3 (INVITROGEN™ Corp.). Selected coding and non-coding sequences were deleted or otherwise mutated (e.g., by nucleotide addition or substitution) within the plasmid vector, using standard techniques, so that only the desired gag and pol polyproteins were expressed. If not deleted from the vector, HIV sequences not to be expressed (e.g., sequences encoding pol reverse transcriptase (RT) and integrase (IN) proteins, env proteins, accessory genes and cis-acting non-coding sequences (e.g., export elements and LTR sequences)) were mutated so as to no longer have sufficient homology with nucleotide sequences contained in any of plasmids pVpr-RTIN, pENV or pΨ described below. A suitable promoter, such as the CMV promoter, also was cloned into the vector upstream of the gag^pol coding sequences if not already present in the plasmid backbone. A map of pgag^pol is shown in FIG. 1.

Plasmid pVpr-RTIN

Figure 2:
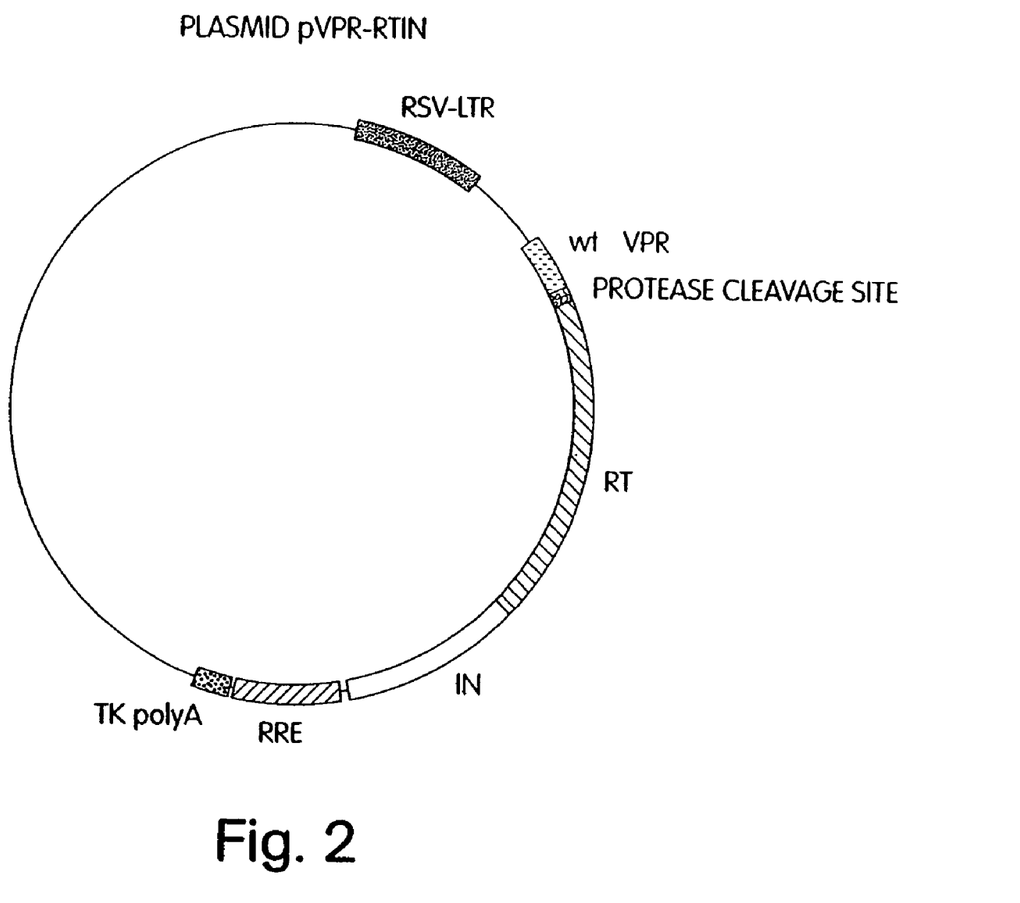

Plasmid pVpr-RTIN was designed to encode a Vpr (or Vpx) fusion protein which contains the remaining portion of the HIV pol polyprotein not encoded by plasmid pgag^pol. Specifically, pVpr-RTIN encoded a fusion protein containing Vpr (which could have been replaced with Vpx), or portions thereof which bind to p6, and pol reverse transcriptase (RT) and integrase (IN). The RT and IN coding sequences were preceded upstream by a protease cleavage site, as shown in FIG. 2. Once expressed in packaging cells, the Vpr (or Vpx) fusion protein associates via p6 with assembled HIV virions produced from gag on pgag^pol. This allows the RT and IN proteins fused to the Vpr to be packaged into the core virions. Thus, Vpr (or Vpx) acts to target or "piggyback" RT and IN proteins to assembling viral particles at the inner face of the plasma membrane, where gag polyprotein precursors direct such viral assembly.

To construct pVpr-RTIN, expression plasmids containing the desired lentiviral coding sequences were constructed as described for pgag^pol (e.g., by mutating HIV sequences contained within PNLENV-1 following cloning into an appropriate expression construct). The Vpr (or Vpx) coding sequence was then be cloned into the plasmid in frame with the pol coding sequences contained therein (e.g., RT and IN). This was done by first performing PCR on a plasmid containing the complete VPR coding sequence, such as SCVCMV (Yau et al. (1995) *J. Virol* 69: 7032-7044). This allowed a Kozak sequence to be placed at the start of the VPR (or Vpx) coding sequence and a Bgl 2 site at the very end of VPR coding sequence, as well as the creation of mutant VPR vectors for reduced cytotoxicity. For example, replacement of GGG (GLY at amino acid position 75) with AAC (ASN), or deletion of the Vpr coding sequence so as to only encode N-terminal amino acids 1-88 (Yau et al. (1995), supra.) has been shown to reduce toxicity of the Vpr protein in cells. The resulting amplified Vpr (or Vpx) construct was then cloned into the plasmid containing the partial pol coding sequence in frame with e.g., the RT and IN coding sequences, keeping in mind and maintaining the 33 base pair protease cleavage (PR) site which precedes IN. Other HIV and non-HIV PR sites also can be used in place of the PR site immediately preceding IN. For example, the HIV-1 protease cleavage site having the amino acid sequence VSQNYPIV (SEQ ID NO:1), located in the junction between HIV-1 p16$^{GAG}$ and p24$^{GAG}$, can be used. For example, the HIV-1 protease cleavage site having the amino acid sequence VSQNYPIV (SEQ ID NO:1), located in the junction between HIV-1 p16$^{GAG}$ and p24$^{GAG}$, can be used. Alternatively, the HIV-1 protease cleavage site having the amino acid sequence ARULAEA (SEQ ID NO:2), located in the junction between HIV-1 p24$^{GAG}$ and p2$^{GAG}$, can be used. A map of plasmid pVpr-RTIN is shown in FIG. 2.

Plasmid pENV

Plasmid pENV was designed to encode the envelope proteins intended for the recombinant lentivirus. These proteins are necessary to form virion particles and dictate the range of host cells which can be infected (and thus transformed) using the recombinant lentivirus. If a non-lentiviral (e.g., non-HIV) env gene is used in pENV, then the resulting packaging cell line will produce pseudotyped lentiviral virions. For example, the coding sequence for the vesicular stomatitis virus glycoprotein (VSVg) can be is used in place of the HIV env gene. This provides the advantages of conferring a broader (pantropic) host range upon the recombinant lentivirus and higher stability, allowing for viral particle concentration by ultracentrifugation.

Figure 3:
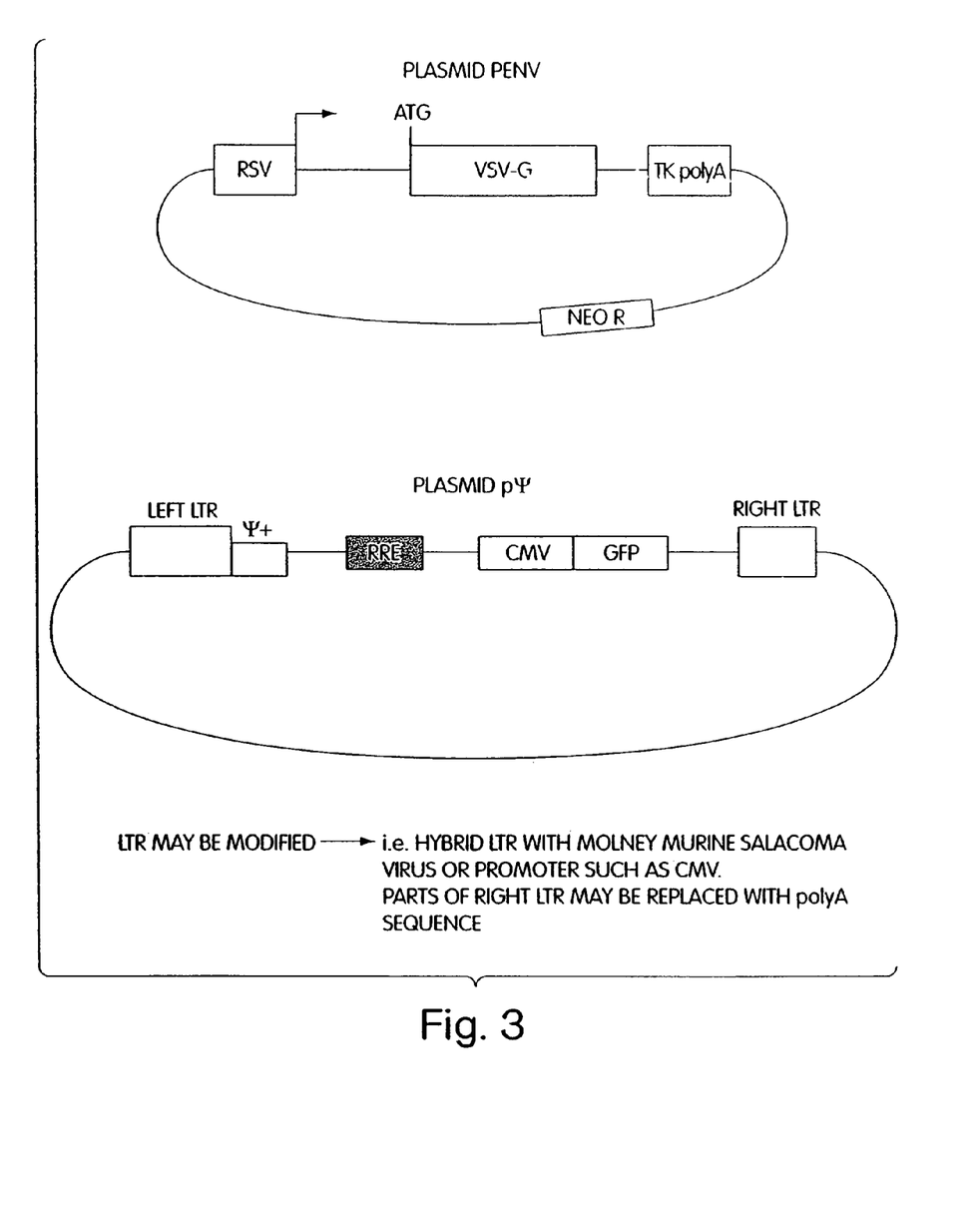
Figure 4:
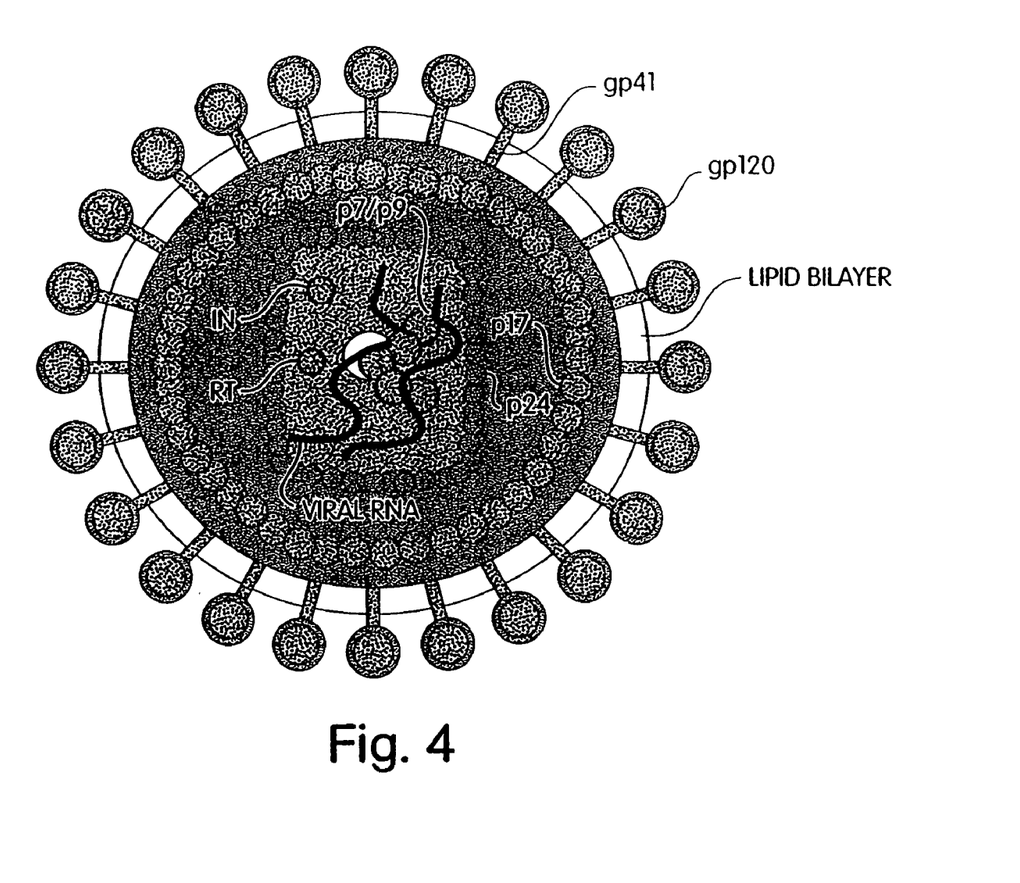
FIG. 4 shows the molecular structure of the HIV virus, including env proteins (gp41 and gp120), gag proteins (p7/p9, p17 and p24) and pol proteins (IN, RT).

To prepare pENV, a desired env coding sequence (e.g., HIV from PNLENV-1 or VSVg) was cloned into one or more suitable expression vectors using standard cloning techniques. The env coding sequence was preceded upstream by a suitable promoter (e.g., an inducible promoter, such as the RSV promoter) and downstream by a polyadenylation signal, as shown in FIG. 3. pENV can also contain a selection marker, such as the neomycin (neo) resistance gene.

Plasmid pΨ

Plasmid pΨ was designed to contain minimal long terminal repeat (LTR) and packaging sequences (Ψ) necessary for packaging of RNA transcribed from pΨ into lentiviral virions, along with a transgene of interest (i.e., a therapeutic gene to be used in human gene therapy). The left (5') LTR acts as a promoter and the right (3') LTR acts as a polyadenylation sequence. When constructing pΨ using lentiviral (e.g., HIV)-based vectors, it is preferable to replace the lentiviral LTR sequences with functionally similar sequences from other viruses. This reduces the likelihood of recombination (e.g., with plasmids pgag^pol, pVpr-RTIN and pENV) and increases the safety of the packaging cell line. For example, a hybrid 5' LTR can be used which replaces a portion of the HIV 5'LTR with the CMV promoter or an LTR from a different retrovirus (e.g., MuLV or MuSV), and a hybrid 3' LTR can be used which replaces a portion of the HIV 3' LTR with a retroviral or rabbit β-globin polyadenylation sequence. Plasmid pΨ also preferably contains an RNA export element (e.g., the HIV Rev responsive element (RRE) (Cullen et al. (1991) *Science* 16: 346-350; Rosen et al. (1990) *AIDS*4: 499-509) or the HBV post-transcriptional regulatory element (PRE) (Huang et al. (1995) *Molec. and Cell. Biol.* 15(7): 3864-3869), which causes export of RNA out of the host cell nucleus into the cytoplasm, and a marker gene (e.g., GFP), all as shown in FIG. 3.

Plasmid pΨ was constructed as described above for plasmids pgag^pol, pVpr-RTIN and pENV by e.g., subcloning HIV LTR, Ψ and RRE (e.g., from pNLENV-1) into a suitable backbone, such as pUC19. Standard techniques were employed to prepare hybrid LTRs by, for example, cloning suitable promoter and polyadenylation sequences into HIV LTR sequences, and deleting appropriate portion of the HIV LTRs. A suitable restriction site for the cloning of heterologous cDNAs (i.e., transgenes) also was added to pΨ, followed by insertion of a desired therapeutic gene (e.g., human β-globin).

Cytotoxicity

In constructing the plasmids described above, additional steps can be taken to address potential toxicity to cells from expression of viral proteins, such as VPR and viral proteases. In one approach, the coding sequences for these proteins can be deleted so as to encode only the minimum portions of the proteins necessary for function (e.g., VPR/p6 binding domains). For example, it is known that expression of full-length VPR can be toxic to cells, but that a truncated form of the protein containing only the first 88 N-terminal amino acids reduces cytotoxicity of the protein, without affecting its function (i.e., its ability to bind to p6). Thus, in one approach, plasmids of the invention encode a truncated, less toxic VPR protein.

In another approach, cytotoxicity is addressed by using conventional repressor elements in the plasmids of the invention. For example, the TET-Regulated Expression System (GIBCO BRL™ Inc.) or LACSWITCH™ Inducible Mammalian Expression System (STRATAGENE™) can be used. Briefly, in the *E. coli* lactose operon, the Lac repressor binds as a homotetramer to the lac operator, blocking transcription of the lac2 gene. Inducers such as allolactose (a physiologic inducer) or isopropyl-β-D-thiogalactoside (IPTG, a synthetic inducer) bind to the Lac repressor, causing a conformational change and effectively decreasing the affinity of the repressor for the operator. When the repressor is removed from the operator, transcription from the lactose operon resumes.

The LACSWITCH™ Inducible Mammalian Expression System utilizes a vector system in which several elements of the lactose operon have been modified for use in eukaryotic cells for the control of gene expression. This method for inducible expression of exogenous genes in eukaryotic cells consists of a eukaryotic Lac-repressor expressing vector, p3'SS and two eukaryotic lac operator containing vectors pOP13CAT and pOPRSVICAT, each available from STRATAGENE™, into which the lentiviral genes of interest can be inserted by cloning. These vectors are transfected into cultured cells where expression of the lentiviral genes is repressed until an inducer, such as IPTG, which permits induction in 4-8 hours.

In yet another approach, selective expression of lentiviral genes contained within the plasmids of the invention can be achieved by cloning in a cre/lox repressor system upstream of coding sequences. Specifically, a polystop signal is inserted between the gene(s) to be selectively expressed and their promoter. The polystop signal is flanked by two loxP1 sites (Sauer (1993) *Methods in Enzymology* 225:890-900). Upon contact with cre recombinase, the lox sites will recombine and delete the polystop signal, allowing the promoter to act in cis to turn on expression of the gene(s). This approach has the dual advantage of allowing plasmids of the invention encoding toxic proteins to remain in packaging cells without toxic side effects, and increasing their safety because the plasmids can remain in culture for longer periods of time without producing virus.

To insert a cre/lox repressor system into plasmids, oligos can be used to clone two lox sites spanning a polystop signal into, e.g., pgag^pol upstream of the gag^pol coding sequence but downstream of the promoter sequence, as shown in FIG. 1.

Cell Transfection, Infection and Selection

To create packaging cells, a suitable cell line is co-transfected with Plasmids 1-3 which collectively encode the viral proteins necessary to form helper free, replication deficient lentiviral virions. Plasmid 4 can then be transfected onto the packaging cells to create a producer cell line (i.e., which produces virions which have packaged Plasmid 4).

Any suitable cell line can be used as a packaging cell line. For example, human 293T cells (kidney fibroblasts) can be used. These cells can be grown and transfected as described by Pear et al. (1993) *PNAS* 90:8392-8396 and Danos et al. (1988) *PNAS* 85:6460-6464. Briefly, cells can be grown at 37° C. with 5% $CO_2$/95% air in DMEM supplemented with 10% heat inactivated calf serum (CS), 4.5 mg/ml glucose, 2.0 mM glutamine, 100 units/ml penicillin and 100 µg/ml streptomycin.

Plasmid DNA can be prepared by the QIAGEN™ procedure (QIAGEN™, Inc.) and transfected into cells using, for example, the calcium phosphate method (5'3', Inc.). Following transfection of Plasmids 1-3 into cells, colonies can be screened for using 320 µml hygromycin B (CALBIOCHEM™). Colonies can be picked, expanded, and screened for reverse transfectase activity as described in Goff et al. (1981) *J. Virol.* 38:239-248), and for infectivity (following transient transfection with the fourth plasmid) by assaying for e.g., GFP by fluorescence-activated cell sorting (FACS) using the green fluorescence protein (GFP, from CLONTECH™), or for β-gal expression using, for example, a β-galactosidase mobilization assay as described by Pear et al. (1993), supra. and Danos et al. (1988), supra. Infectivity can be tested on various cell types, dividing and non dividing.

What is claimed is:

1. A method of producing a packaging cell line capable of producing a recombinant, helper-free retrovirus, comprising transfecting a host cell with:
- a first vector comprising a retroviral gag gene, wherein said gag gene encodes retroviral matrix, capsid and nucleocapsid proteins;
- a second vector comprising a portion of a retroviral pol gene, fused to a Vpr or Vpx gene, wherein said portion of said pol gene encodes a retroviral protease;
- a third vector comprising the remainder of the retroviral pol gene not contained in said second vector, fused to a Vpr or a Vpx gene, wherein said remainder of said pol gene encodes a retroviral reverse transcriptase and a retroviral integrase; and
- a fourth vector comprising a viral env gene.

2. The method of claim 1, wherein transcription of any one of said genes within said vectors is directed by an inducible promoter.

3. The method of claim 2 further comprising the step of contacting said host cell with an agent which induces said promoter.

4. The method of claim 1 wherein said retrovirus is a lentivirus.

5. The method of claim 4, wherein said lentivirus is selected from the group consisting of HIV-1, HIV-2, SIV, FIV and EIV.

6. The method of claim 1, further comprising transfecting the host cell with retroviral accessory genes.

7. The method of claim 1, wherein said remainder of said retroviral pol gene further comprises a protease cleavage site upstream from said reverse transcriptase and said integrase.

8. The method of claim 1, wherein said third vector further comprises a retroviral Vif gene.

9. The method of claim 1, wherein said viral env gene within said third vector encodes an envelope protein selected from a virus selected from the group consisting of a Type C retrovirus, a lentivirus and Vesicular Stomatitis Virus.

10. The method of claim 1, wherein any of the first, second, third or fourth vectors further comprise an RNA export element.

11. The method of claim 10, wherein said RNA export element is the reverse response element (RRE) from human immunodeficiency virus (HIV).

12. The method of claim 1, wherein any of the first, second, third or fourth vectors further comprise a marker gene.

13. The method of claim 4, wherein said lentivirus is HIV.

14. The method of claim 1, wherein transcription of any one of said genes within said vectors is induced by contact of Cre recombinase with one or more Lox sites contained in said vector.

* * * * *